(12) United States Patent
Papp

(10) Patent No.: US 7,976,574 B2
(45) Date of Patent: Jul. 12, 2011

(54) DELIVERY SYSTEM WITH VARIABLE DELIVERY RATE FOR DEPLOYING A MEDICAL DEVICE

(75) Inventor: John E. Papp, Temecula, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 243 days.

(21) Appl. No.: 12/188,822

(22) Filed: Aug. 8, 2008

(65) Prior Publication Data
US 2010/0036472 A1 Feb. 11, 2010

(51) Int. Cl.
*A61F 2/06* (2006.01)
(52) U.S. Cl. .................................................. 623/1.11
(58) Field of Classification Search .................. 606/108, 606/191, 192, 194, 198, 200, 144–148; 623/1.11, 623/1.12, 1.23; 600/585; 242/375.1, 375.3, 242/376, 395, 407
See application file for complete search history.

(56) References Cited

U.S. PATENT DOCUMENTS

| | | | |
|---|---|---|---|
| 706,606 A * | 8/1902 | Spriggs | 242/388.2 |
| 4,624,243 A | 11/1986 | Lowery et al. | |
| 4,665,918 A | 5/1987 | Garza et al. | |
| 5,346,498 A | 9/1994 | Greelis et al. | |
| 5,391,172 A | 2/1995 | Williams et al. | |
| 5,501,654 A | 3/1996 | Failla et al. | |
| 5,507,768 A | 4/1996 | Lau et al. | |
| 5,571,168 A | 11/1996 | Del Toro | |
| 5,591,172 A | 1/1997 | Bachmann et al. | |
| 5,593,412 A | 1/1997 | Martinez et al. | |
| 5,683,451 A | 11/1997 | Lenker et al. | |
| D387,863 S | 12/1997 | Herman et al. | |
| 5,707,376 A | 1/1998 | Kavicladze et al. | |
| 5,733,267 A | 3/1998 | Del Toro | |
| 5,833,694 A | 11/1998 | Poncet | |
| 5,868,711 A | 2/1999 | Kramer et al. | |
| 5,906,649 A | 5/1999 | Genzel et al. | |
| 5,920,975 A | 7/1999 | Morales | |
| 5,944,727 A | 8/1999 | Ahari et al. | |
| 5,968,052 A | 10/1999 | Sullivan, III et al. | |
| 6,146,415 A | 11/2000 | Fitz | |
| 6,165,184 A | 12/2000 | Verdura et al. | |
| 6,183,443 B1 | 2/2001 | Kratoska et al. | |
| 6,190,360 B1 | 2/2001 | Iancea et al. | |
| D439,664 S | 3/2001 | Cuschieri et al. | |
| 6,203,550 B1 | 3/2001 | Olson | |
| 6,238,402 B1 | 5/2001 | Sullivan et al. | |
| 6,254,611 B1 | 7/2001 | Vrba | |
| 6,391,050 B1 | 5/2002 | Broome | |
| 6,391,051 B2 | 5/2002 | Sullivan, III et al. | |
| 6,514,261 B1 | 2/2003 | Randall et al. | |
| 6,520,983 B1 | 2/2003 | Colgan et al. | |
| 6,527,779 B1 | 3/2003 | Rourke | |

(Continued)

FOREIGN PATENT DOCUMENTS
WO WO 99/49808 10/1999
(Continued)

*Primary Examiner* — Anhtuan Nguyen
*Assistant Examiner* — Katherine M Shi
(74) *Attorney, Agent, or Firm* — Fulwider Patton LLP; Abbott Vascular; Jonathan Feuchtwang

(57) ABSTRACT

A delivery system utilizes a handle assembly including an actuating mechanism capable of initially providing sufficient mechanical advantage to overcome static friction when initiating deployment of the medical device. The actuating mechanism includes components which help to increase the speed of deployment as the physician continues to manipulate the actuating mechanism.

24 Claims, 11 Drawing Sheets

U.S. PATENT DOCUMENTS

| | | |
|---|---|---|
| 6,599,296 B1 | 7/2003 | Gillick et al. |
| 6,602,280 B2 | 8/2003 | Chobotov |
| 6,669,716 B1 | 12/2003 | Gilson et al. |
| 6,755,854 B2 | 6/2004 | Gillick et al. |
| 6,866,669 B2 | 3/2005 | Buzzard et al. |
| D509,589 S | 9/2005 | Wells |
| 6,939,352 B2 | 9/2005 | Buzzard et al. |
| D518,175 S | 3/2006 | Hardin et al. |
| 7,122,050 B2 | 10/2006 | Randall et al. |
| D533,274 S | 12/2006 | Visconti et al. |
| D536,784 S | 2/2007 | Bacher et al. |
| D553,242 S | 10/2007 | Fedenia et al. |
| 2003/0144671 A1 | 7/2003 | Brooks et al. |
| 2004/0006380 A1 | 1/2004 | Back et al. |
| 2004/0117000 A1 | 6/2004 | Ruetsch |
| 2004/0148009 A1 | 7/2004 | Buzzard et al. |
| 2005/0060016 A1 | 3/2005 | Wu et al. |
| 2005/0080476 A1 | 4/2005 | Gunderson et al. |
| 2005/0273151 A1 | 12/2005 | Fulkerson et al. |
| 2006/0074477 A1 | 4/2006 | Berthiaume et al. |
| 2007/0032860 A1 | 2/2007 | Brooks et al. |
| 2007/0088421 A1 * | 4/2007 | Loewen ............ 623/1.11 |
| 2009/0210046 A1 | 8/2009 | Shumer et al. |
| 2010/0036472 A1 | 2/2010 | Papp |

FOREIGN PATENT DOCUMENTS

| | | |
|---|---|---|
| WO | 2007/022395 A1 | 2/2007 |
| WO | 2007/044929 A1 | 4/2007 |

* cited by examiner

DELIVERY SYSTEM WITH VARIABLE DELIVERY RATE FOR DEPLOYING A MEDICAL DEVICE

BACKGROUND

The present invention relates generally to delivery systems and methods for deploying medical devices and, more particularly, to delivery systems and methods for their use to accurately deploy medical devices, such as a stent, a vascular stent-graft and the like, in a body vessel of a patient for the treatment of stenosis, aortic aneurysms and other afflictions which may strike body vessels. The present invention also can be used to deliver medical devices for arthroscopic surgery and other surgical procedures.

Stents are generally cylindrically shaped devices which function to hold open and sometimes expand a segment of a blood vessel or other arterial lumen, such as coronary artery. Stents are usually delivered in a compressed condition to the target site and then deployed at that location into an expanded condition to support the vessel and help maintain it in an open position. They are particularly suitable for use to support and hold back a dissected arterial lining which can occlude the fluid passageway there through. Stents are particularly useful in the treatment and repair of blood vessels after a stenosis has been compressed by percutaneous transluminal coronary angioplasty, percutaneous transluminal angioplasty, or removed by atherectomy or other means, to help improve the results of the procedure and reduce the possibility of restenosis. Stents, or stent like devices, are often used as the support and mounting structure for implantable vascular grafts which can be used to create an artificial conduit to bypass the diseased portion of the vasculature, such as an abdominal aortic aneurism.

A variety of devices are known in the art for use as stents and have included coiled wires in a variety of patterns that are expanded after being placed intraluminally on a balloon catheter; helically wound coiled springs manufactured from an expandable heat sensitive metal; and self expanding stents inserted into a compressed state for deployment into a body lumen. One of the difficulties encountered in using prior art stents involve maintaining the radial rigidity needed to hold open a body lumen while at the same time maintaining the longitudinal flexibility of the stent to facilitate its delivery through the often tortuous paths of the body lumen.

Prior art stents typically fall into two general categories of construction. The first type of stent is expandable upon application of a controlled force, often through the inflation of the balloon portion of a dilatation catheter which, upon inflation of the balloon or other expansion means, expands the compressed stent to a larger diameter to be left in place within the artery at the target site. The second type of stent is a self expanding stent formed from shape memory metals or super-elastic nickel titanium alloys, which will automatically expand from a compressed state when the stent is advanced out of the distal end of the delivery catheter, or when a restraining sheath which holds the compressed stent in its delivery position is retracted to expose the stent.

Some prior art stent delivery systems for delivery and implanting self-expanding stents include an inner member upon which the compressed or collapsed stent is mounted and an outer restraining sheath which is initially placed over the compressed stent prior to deployment. When the stent is to be deployed in the body vessel, the outer sheath is moved in relation to the inner member to "uncover" the compressed stent, allowing the stent to move to its expanded condition. Some delivery systems utilize a "push pull" type technique in which the outer sheath is retracted while the inner member is pushed forward. Another common delivery system utilizes a simple pull-back delivery system in which the self-expanding stent is maintained in its compressed position by an outer sheath. Once the mounted stent has been moved to the desired treatment location, the outer sheath is pulled back via a deployment handle located at a remote position outside of the patient, which uncovers the stent to allow it to self expand within the patient. Still other delivery systems use an actuating wire attached to the outer sheath. When the actuating wire is pulled to retract the outer sheath and deploy the stent, the inner member must remain stationary, preventing the stent from moving axially within the body vessel.

Controlled deployment of the stent can be a desirable feature in various applications. This can be particularly true when attempting to deploy a self-expanding stent which may tend to spring forward as the sheath is being removed. Moreover, stents and stent-grafts are being made in longer lengths for implantation in peripheral vessels, such as the arteries of the leg, to treat conditions such as Peripheral Arterial Disease (PAD). Such longer stents often require additional deployment time in contrast to shorter stents which are implanted in the coronary arteries. When a long stent is deployed from a catheter utilizing a retractable outer sheath, the initial deployment force is high since static friction between the stent and the outer sheath, along with the remaining catheter components, needs to be overcome. Static friction, sometimes referred to as "striction," between the retraining sheath and the stent can pose a problem since a high, initial deployment force must be applied to the actuating mechanism of the delivery system in order to commence retraction of the sheath to uncover the stent. Therefore, it is important that the delivery system provide at least some amount of "mechanical advantage" when the system's actuating mechanism is initially engaged so that the physician is not struggling to get the retraction started. Mechanical advantage refers to the ratio of the output force of an actuator to the input force and is achieved when the ratio is greater than one. The larger the mechanical advantage, the less force is needed to initiate movement of the actuating mechanism. Moreover, the delivery system usually requires a slower and more controlled deployment rate when initially retracting the outer sheath to initiate deployment of the stent in the body vessel. This is to ensure that the stent is placed accurately in the body vessel.

After the stent is somewhat deployed, the amount of deployment force needed to retract the remaining outer sheath is reduced since dynamic frictional forces are typically lower than static frictional forces. After the sheath starts to move, the deployment force needed to continue retraction drops off quickly to less than about 60% of then initial deployment force. Moreover, once the distal-most portion of the stent has made some wall apposition with the body vessel, it is advantageous to quickly deploy the remainder of the stent. Therefore, it may be desirable to employ a delivery system which provides additional delivery speed once static friction is overcome, especially when the length of the stent or graft is quite long. Accordingly, an ideal delivery system should reduce the amount of actuating motions imparted by the user once retraction has begun. Accordingly, it has been found to be desirable to have a delivery system which provides sufficient control and mechanical advantage for initially deploying the medical device which then translates to increased delivery speed once retraction has begun in order to assist the physician in quickly and accurately deploying the medical device.

The present invention disclosed herein satisfies these and other needs.

SUMMARY OF THE INVENTION

Briefly and in general terms, the present invention is directed towards delivery systems and methods of their use for controlling deployment of a medical device, such as a stent, stent-graft and the like, within a body lumen of a patient. The present invention provides a deployment rate that starts initially slow, with high torque, and quickly transforms to high deployment speed. At the high deployment speed, less torque is available, however, less torque is needed since the high static frictional force at the start of deployment has been overcome. The present invention thus provides the physician with a deployment/delivery system that reduces the amount of force initially need to start deployment and reduces the number of actuating strokes need to rapidly deploy the medical device. This system also should shorten the time of the interventional procedure.

In one embodiment, the delivery system utilizes a handle assembly including an actuating mechanism capable of initially providing sufficient mechanical advantage to overcome static friction when initiating deployment of the medical device. The actuating mechanism includes components which help to increase the speed of deployment as the physician continues to manipulate the actuating mechanism. The handle assembly includes an actuating mechanism coupled to a retractable sheath that extends over the medical device. The actuating mechanism includes a flexible elongate member, for example, a belt or wire, having one end coupled to the retractable sheath and the other end coupled to a rotatable, wind-up member, such as a drum or spool. The wind-up member is rotatable via the actuating mechanism to allow a portion of the flexible elongate member (for example, a belt) to wind thereon to cause longitudinal movement of the retractable sheath. The actuating mechanism has a high initial mechanical advantage when the sheath is first moved from a resting, delivery position in which the retractable sheath is coaxially disposed over the entire medical device.

The actuating mechanism is associated with a speed-increasing member which quickly increases the speed by which the retractable sheath moves as the flexible elongate member is being wound about the wind-up member. In turn, the speed by which the retraining sheath is retracted from the medical device is also increased, resulting in overall quicker deployment of the medical device. Therefore, the deployment rate increases with the same input speed being applied by the user.

In one aspect, the speed-increasing member is a component coupled to the wind-up member which quickly and effectively increases the overall diameter of the wind-up member as it is being rotated via the actuating mechanism. In one aspect, the speed-increasing member is a cam or a plurality of linked cams coupled to the wind-up member.

In another aspect of the present invention, the wind-up member can be configured with a speed-increasing member formed as a substantially conical or cone shape which allows the elongate member to rapidly or slowly move as the wind-up member is being rotated. In this aspect, the elongate member could be either a belt or wire which winds up on the conical portion of the wind-up member. The shape of this conical portion could be varied to increase or decrease the speed by which the elongate member will be wound about the wind-up member. For example, the conical portion of the wind-up member could initially have an increasing radius which results in initial enhanced speed and the radius could be later decreased to slow down the speed by which the elongate member is wound about the wind-up member. The wind-up member could include grooves formed in the surface which guides the elongate member along the conical portion as the elongated member is being wound about the wind-up member.

In another aspect of the invention, the speed-increasing member is a component, for example, a cam or cam-like structure, associated with the elongate member, rather than the wind-up member. In this aspect of the invention, the elongate member provides the means by which speed of retraction can be quickly increased. Normally, when an elongate member, such as a belt or wire, winds around a rotating object, such as a drum, it overlaps portions of the elongate member which have already been wrapped around the drum. As the build-up of windings continues, the radius of the built-up windings increases. This, in turn, results in a decrease in the amount that the drum needs to be rotated in order to retract a length of the elongate member. The deployment rate increases given the same input speed. The present invention utilizes this principle by quickly increasing the amount of build up (increasing the radius) of the windings to quickly increase the speed by which the elongate member is wound. The resulting increased speed in winding the elongate member around the wind-up member, in turn, increases the speed by which the coupled restraining sheath will be retracted and the medical device deployed.

Therefore, small displacements of the actuating mechanism by the user will result in large displacements of the restraining sheath. In this aspect of the present invention, the speed-increasing member can be a component, such as cam or similar structure, which is attached to, or integrally formed with, the elongate member. As the wind-up member is rotated, the radius of the windings increases dramatically as the speed-increasing member winds about the wind-up member. The speed-increasing member effectively increases the radius of the windings much faster than a system which only utilizes a uniformly thick elongate member. Accordingly, the speed by which the elongate member is wound up by the actuating mechanism greatly increases given the same input speed or motion by the physician. In another aspect of the present invention, a speed-increasing member could be associated with both the wind-up member and the elongate member to greatly increase the speed by which the outer sheath will be retracted as the physician manipulates the actuating mechanism.

The actuating mechanism can include a thumbwheel assembly operatively connected to a retractable outer sheath which can be retracted via thumb motions by the physician in order to deploy the medical device. For example, the wind-up member (drum) can be coupled to this thumbwheel. The speed-increasing components can be, in turn, coupled to the wind-up member or the elongate member, or both. It should be appreciated that other actuating mechanisms could also be used to rotate the wind-up mechanism, including, but not limited to an actuator that provides a pistol-like trigger that can be repetitively actuated, or a mechanism which uses linear movement of a component to rotate the wind-up member. Such a linear mechanism could utilize, for example, a rack and pinion system to translate linear motion to rotational movement of the wind-up member.

In a particular aspect, the present invention includes a handle assembly including a belt attached at one end to a shuttle assembly which is, in turn, coupled to the retractable sheath or other structure enclosing the medical device. Such a shuttle assembly would be configured to move longitudinally within the casing forming the handle.

Accordingly, the present invention contemplates an actuating mechanism for effecting accurate withdrawal of a sheath of the delivery system. In this manner, the operator is provided with enhanced control of the delivery and implantation of a medical device when the actuating mechanism is initially manipulated, along with increased speed of retraction of the sheath as the user continues to deploy the medical device.

These and other features of the present invention become apparent from the following detailed description and the accompanying exemplary drawings.

DETAILED DESCRIPTION OF THE PREFERRED EMBODIMENTS

The present invention relates to a system that delivers and deploys a medical device at a target site within a patient's body, such as a body lumen. For illustration purposes, the following exemplary embodiments are directed to a system for delivering and deploying a self-expanding stent, although it is understood that the present invention is applicable to other medical devices which are implantable in a body lumen as well as other parts of the body. Additionally, the medical device can be either self-expanding or a non self-expanding (balloon expandable). If the stent is balloon expandable, then a balloon catheter would be used to expand the stent at the target location.

Figure 1:
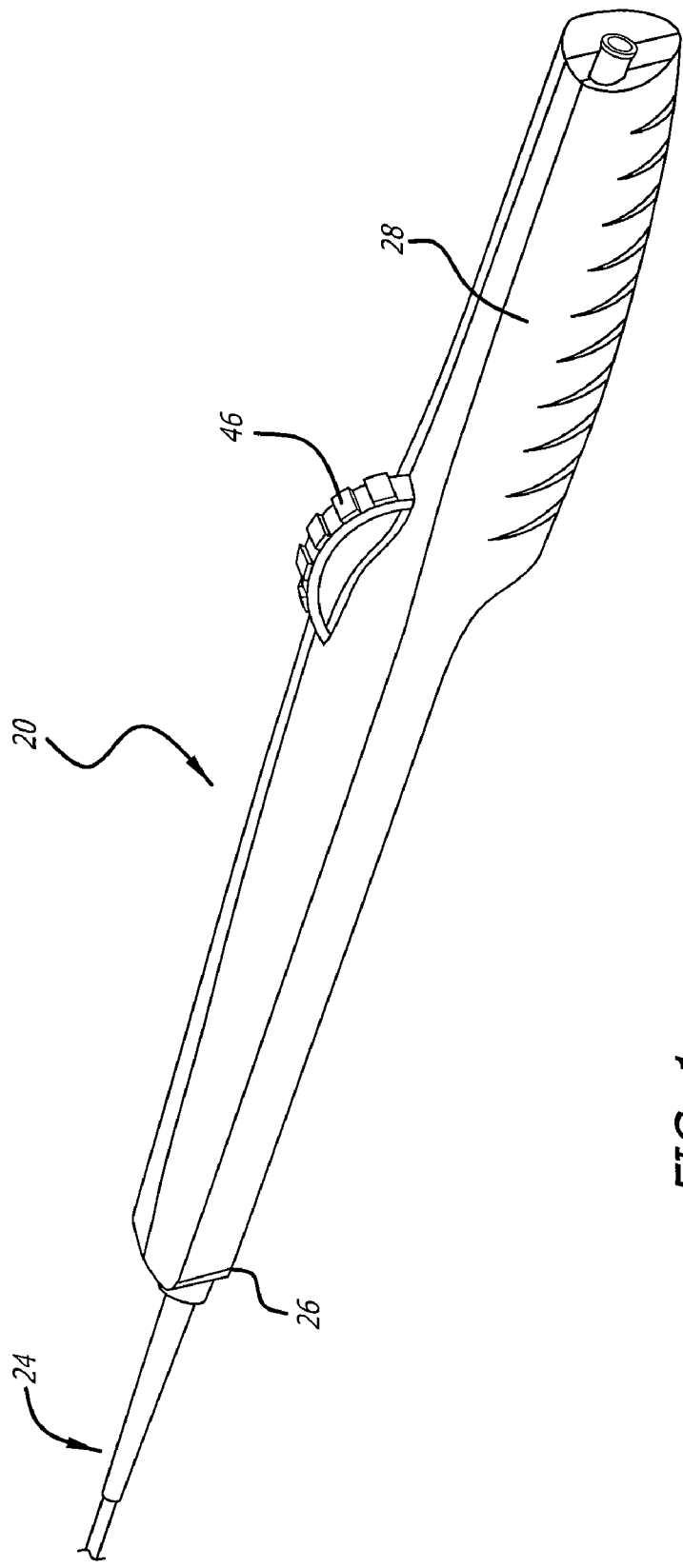
FIG. 1 is a perspective view of a handle assembly of a delivery system made in accordance with the present invention.
Figure 2:
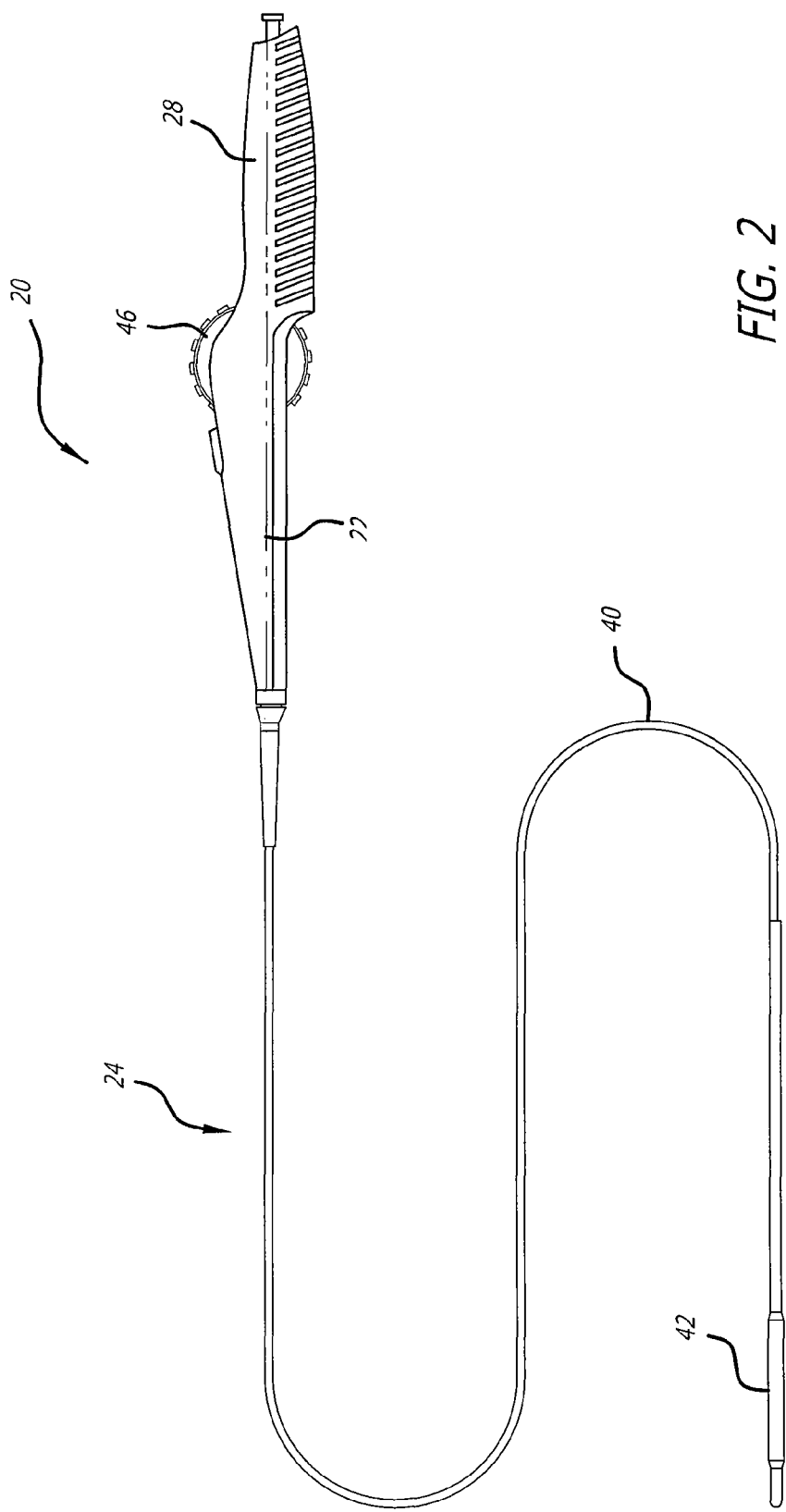
FIG. 2 is a side elevational view depicting the handle portion and catheter portion of a delivery system made in accordance with the present invention.
Figure 3:
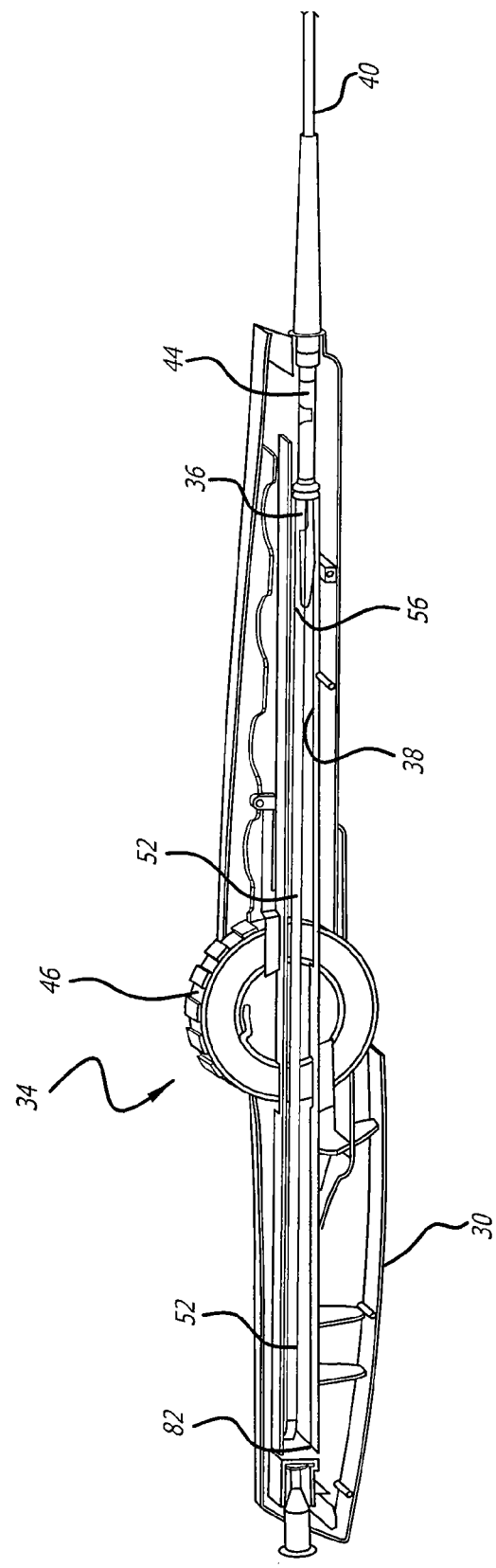
FIG. 3 is a perspective view depicting the delivery system of FIG. 1 with the right handle casing removed.
Figure 4:
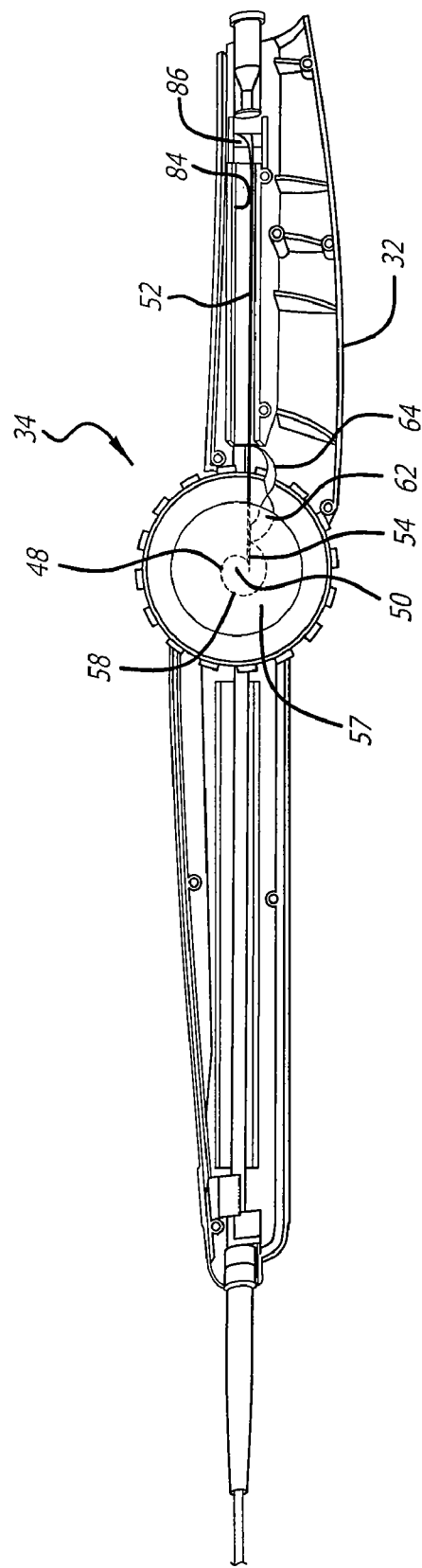
FIG. 4 is a perspective view depicting the delivery system of FIG. 1 with a left handle casing removed.
Figure 5:
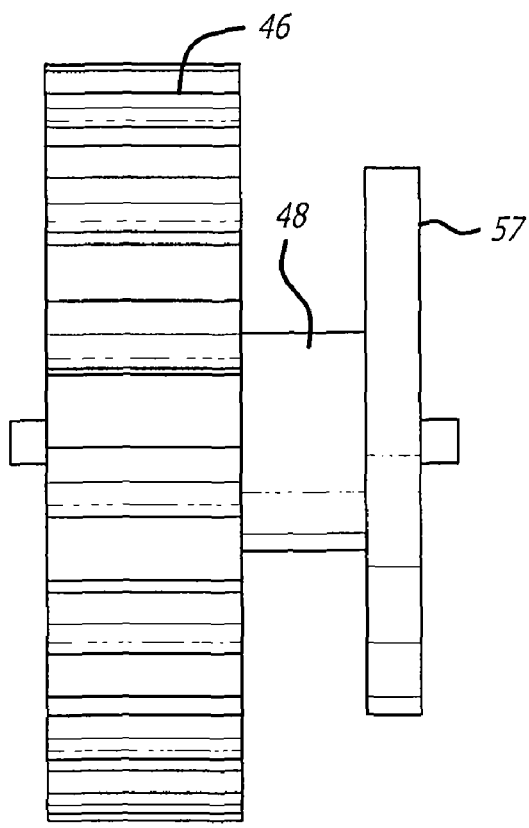
FIG. 5 is a top view depicting a portion of the actuating mechanism used in the delivery system depicted in FIGS. 1-4.

Referring now to FIGS. 1-6, a delivery system 20 with a handle assembly 22 embodying features of the present invention is illustrated. The delivery system includes a catheter portion 24 coupled to the distal end 26 of the handle assembly 22. The handle assembly 22 is generally elongate and includes a gripping portion 28 that comfortably fits in an operator's hand. Additionally, encasing internal components of the handle assembly are a first handle housing 30 (FIG. 3.) which mates with a second handle housing 32 (FIG. 4).

Further, in one aspect, the handle assembly 22 includes an actuating mechanism 34, disclosed in this particular embodiment as a thumbwheel sub-assembly, mounted within the handle housings 30, 32. This actuating mechanism 34 can be actuated to effect longitudinal movement of a shuttle assembly 36 (See FIG. 3) which moves along a channel 38 extending along the entire length of the handle assembly. The thumbwheel assembly is conveniently located at a mid-section of the handle assembly 22 so that an operator can hold the gripping portion 28 while using his/her thumb on top, or thumb on top and finger below, to actuate the thumbwheel assembly.

The actuating mechanism 34 of the handle assembly 22 is coupled to an outer restraining sheath 40 which is movable by the actuating mechanism 34 in order to deploy a medical device, such as a self-expanding stent (not shown), which is covered by the restraining sheath 40. As can be seen in FIG. 2, the outer restraining sheath 40 forms a part of the catheter portion 24 and includes a distal end portion 42 designed to extend over the stent to maintain the stent in a collapsed or unexpanded position. The stent could be mounted on an inner catheter (not shown) which also forms a part of the catheter portion 24. The inner catheter would extend from the handle assembly to the distal end of the catheter portion 24. When the stent is ready to be deployed at a target location, the physician simply holds the gripping portion 28 of the handle assembly 22 and utilizes his/her thumb above or thumb and finger below to actuate the thumb wheel assembly. The outer restraining sheath 40 includes a proximal end portion 44 coupled to the actuating mechanism 34 of the handle assembly 22 to allow the sheath 40 to be retracted approximately in order to deploy the stent.

As can be seen in FIG. 3, one way to couple the restraining sheath 40 to the actuating mechanism 34 is by attaching the proximal end portion 44 to the shuttle assembly 36. In this manner, the physician can simply utilize thumb or thumb/finger motions to rotate thumb wheel 46 of the thumbwheel assembly resulting in shuttle 36 and sheath 40 moving proximally from the stent. The shuttle assembly 36 is designed to move within a channel 38 formed in the handle assembly. Since the stent is a self-expanding stent, as the distal portion 42 of the restraining sheath 40 is removed initially from the stent, the distal end of the stent will begin to expand and make contact with the wall of the body vessel in which the stent is being implanted. Thereafter, as the restraining sheath 40 is further retracted from the stent, the remaining portion of the stent will continue to expand to make further contact with the vessel wall.

The actuating mechanism 34 further includes components which help to provide longitudinal motion to the shuttle assembly 36 and, in turn, to the outer restraining sheath 40 as well. As can best be seen in FIGS. 5-7, the actuating mechanism 34 includes a wind-up member 48 coupled to the thumbwheel 46 of the thumbwheel assembly. This wind-up member, shown as a drum 48 or spool, can be rotated via the rotation of the thumbwheel 46 by the user. The drum 48 and thumbwheel 46 can be mounted to a pin 50, shown in FIGS. 5 and 6, which extends from the casing forming the handle assembly to allow these components to rotate. An elongate member, shown as a belt 52, includes an end 54 attached to the drum 48. In this manner, the drum 48 acts as a means for "taking up" the belt 52 as the drum 48 is rotated via the thumbwheel 46 by the user. The other end 56 of the belt 52 is, in turn, coupled to the shuttle assembly 36. Therefore, as the belt 52 winds around the drum 48, the distal end 56 of the belt moves proximally as well and, in turn, moves both the shuttle assembly 36 and the outer restraining sheath 40 proximally. As the belt 52 winds around the drum 48, the number of windings of the belt 52 around the drum 48 will increase which can result in the belt 52 "jumping" off of the drum 48 as the drum is being rotated. To prevent this from occurring, a drum plate 57 is attached to the drum (see FIGS. 4 and 5) to create an abutment which prevents the windings of the belt 52 from slipping off the drum 48 during rotation.

Figure 6:
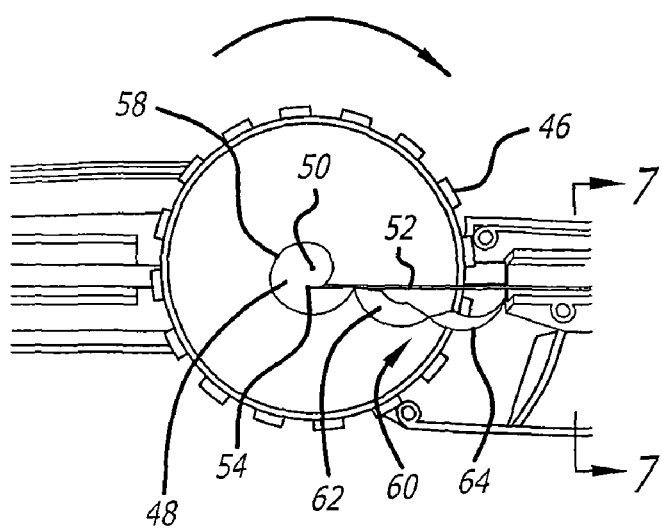
FIG. 6 is a side, elevational view of the actuation mechanism used in the delivery system of FIGS. 1-5 with the drum plate removed to more clearly shown the actuating components.
Figure 7:
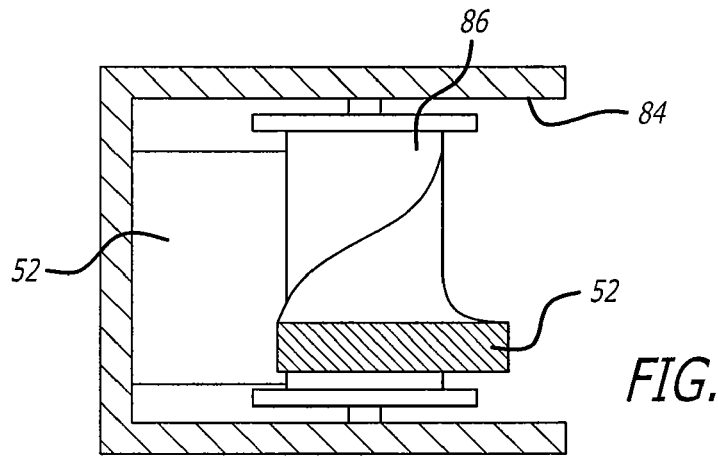
FIG. 7 is a cross-sectional view of a portion of the actuation mechanism taken along line 7-7.

As can be seen in FIG. 6, the plate 57 has been removed to more clearly show some of the components forming the actuating mechanism 34. As can be seen in FIG. 6, the drum 48, in this particular embodiment, has an outer edge 58 in a spiral configuration to produce varying degrees of radius along the edge 58. The function of this spiral-shaped edge will be discussed in greater detail below. As can be seen in FIG. 6, rotation of the thumbwheel 46 in a clockwise direction also causes the drum 48 to rotate in a clockwise direction. A speed-increasing member 60 is coupled to the drum 48 to rapidly increase the speed by which the belt 52 is wound around the drum 48. In the particular embodiment disclosed in FIGS. 1-12, the speed-increasing member 60 is shown as a first cam 62 linked to a second cam 64. For example, the first cam 62 can be pivotally connected to the second cam 64. The features of this speed increasing member will be discussed in greater detail below.

Turn now to FIGS. 6 and 8-13, the function of the drum 48 and the speed increasing cams 62 and 64 are best shown through the progression of rotation of the thumbwheel 46. Initially, in FIG. 6, the delivery system 20 is shown in its delivery condition in which the distal portion 42 of the outer restraining sheath 40 entirely covers the stent. When the actuating mechanism 34 is initially activated by the user, the static frictional forces which exist between the distal portion of the outer restraining sheath 40 and the stent and also between the sheath 40 and other components of the catheter can be quite large which can require the user to exert a large amount of force in order to initiate deployment. This is particularly true when the restraining sheath is positioned in a tight, tortuous portion of the patient's vasculature. In tortuous anatomy, the static friction between catheter components and the sheath can be greater than the friction between the sheath and the stent. Moreover, the stent static friction and catheter static friction are independent and both can be quite high. For these reasons, the present invention is designed to overcome both of these frictional forces. By providing a sufficient amount of mechanical advantage during the initial actuating strokes, the amount of force required by the user to start deploying the stent can be greatly decreased. In the particular embodiment disclosed herein, it is preferable that the radius of the drum 48 be small since a smaller radius in conjunction with the larger radius of the thumbscrew 46 provides a larger amount of mechanical advantage to the user.

Figure 8:
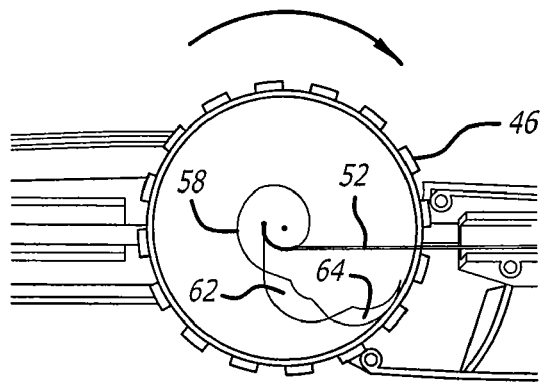
FIGS. 8-13 shows the progression of the actuation mechanism depicted in FIG. 5 as the thumbwheel, drum and cam are rotated in order to move the belt in a proximal direction.

As can be seen in FIG. 6, the end 54 of the belt 52 is attached to the drum 48 at a point where the outer edge 58 of the drum has its smallest radius. Again, the small radius at this initial location helps to provide the needed mechanical advantage to the actuating mechanism 34. FIG. 8 shows a position in which actuation of the thumbwheel 46 has commenced resulting in some rotation of the drum 48. At this position, the radius of the drum 48 in contact with the belt 52 is approximately the same as is shown in FIG. 6. Alternatively, the radius could be more or less than is shown to obtain the desired speed characteristics. This smaller radius again provides initial high mechanical advantage to the actuating mechanism 34 in order to reduce the amount of actuating force needed to start deployment and overcome the static frictional forces associated with the restraining sheath 40 and stent. This initial rotation also results in the distal end 56 of the belt 52 moving proximally to move both the shuttle assembly 36 and the coupled restraining sheath 40. By this point, the actuating mechanism has started to overcome the static frictional forces associated with the delivery system.

Figure 9:
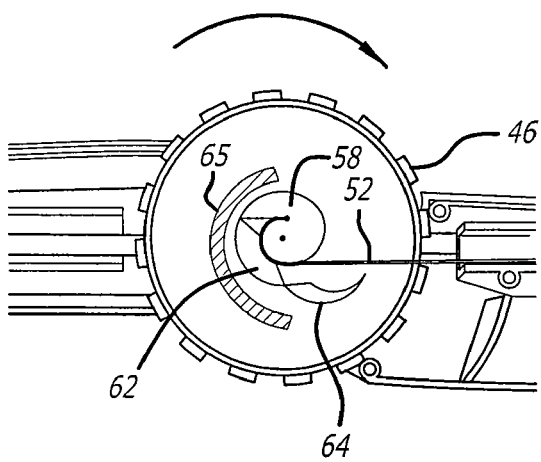
Figure 10:
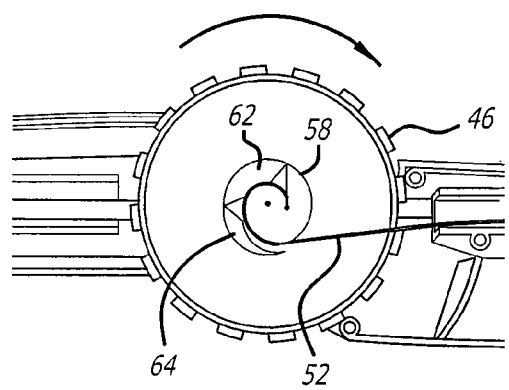

Rotation of the thumbwheel 46 continues as is shown in FIG. 9. As can be seen in this drawing, the belt 52 continues to wind around the small radius of the drum 48. Again, this particular actuation result in high mechanical advantage since the contact between the drum 48 and belt 52 is at the drum's smaller radius. As can best be seen in FIG. 9, the first cam 62, which is rotationally attached to a portion of the drum 48 along its outer edge 58, begins to contact the drum 48 as the belt 52 begins to contact the outer radius of the drum 48. Additionally, while the belt is shown moving the cams into place against the drum, it is also possible to utilizes a fixed guide 65, shown in FIG. 9, which can be formed on the handle to moves the cams 62 and 64 into position. The actuating mechanism has started to overcome the static frictional forces and dynamic frictional forces are coming into play. Since dynamic frictional forces are less than static frictional forces, less torque is now need to continue deployment of the medical device. Further actuation of the thumbwheel (FIG. 10) results in gravity causing the cam 62 to be positioned against the drum 52. The drum 52 now starts to have a progressively larger radius at the outer edge 58 than at the previous section due to the spiral shape located at the outer edge. Again, since the drum 48 has a spiral outer edge, which form a "ramp-like" structure, the radius of the drum 48 will increase causing the belt 52 to wrap more quickly as the user continues to rotate the thumb wheel at a constant rate. The belt 52 will wrap quicker than it did during the initial actuation depicted in FIGS. 6, 8 and 9 given the same rotation rate applied by the user. In this regard, the spiral-shaped outer edge 58 of the drum acts as a speed-increasing member as the drum 48 is being rotated. Also, as can be seen in FIG. 10, the second cam 64 starts to make contact with the belt which remains in contact with the drum 48 in an area where the belt 52 has begun wrapping itself around the drum.

Figure 11:
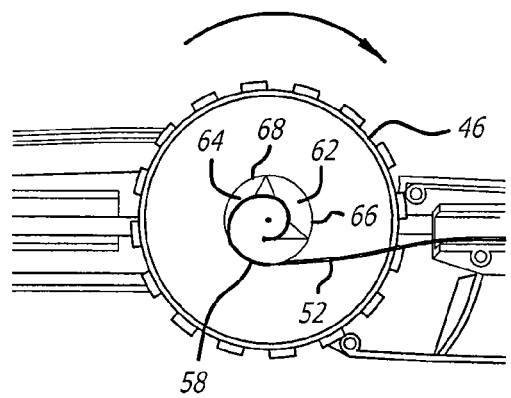
Figure 12:
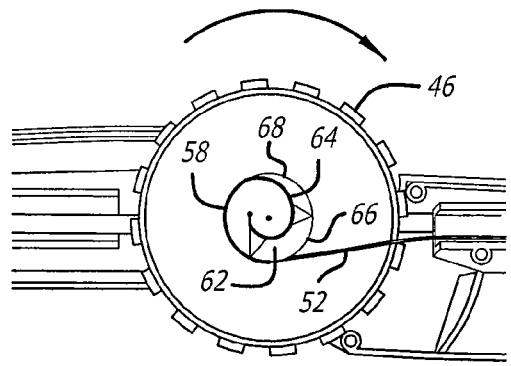
Figure 13:
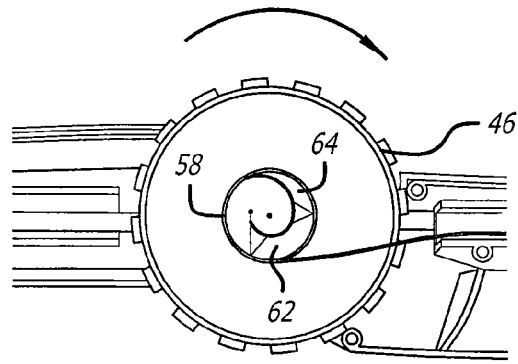

Further actuation of the thumbwheel (FIG. 11) results in the drum 48 and cams 62 and 64 reaching a position where the outer most edges 66 and 68 of cams 62 and 64 combine with the largest, outermost radius of the drum's edge 58 to form a composite outer edge of constant radius. In this fashion, the thumbwheel 46 has been rotated a little more than one full rotation and the speed-increasing member 60 of the present invention has been activated. Moreover, this speed-increasing feature is implemented though the simple rotation of the thumbwheel 46 of the actuating mechanism 34. Now, as can be seen in FIGS. 11-13, the belt 52 will begin wrapping around this newly formed outer radius which also helps to maintain the cams 62 and 64 pressed against the drum 58. Further rotation of the thumbwheel, as shown in FIG. 11, results in the belt 52 beginning to wrap around this larger outer edge. FIG. 11 shows just how larger the radius has changed from the original small radius shown in FIGS. 6 and 8 after just one rotation of the drum 48. As can be seen FIG. 11, in this particular embodiment, one rotation of the thumbwheel 46 results in about the doubling of the effective radius of the drum. This speed-increasing member associated with the wind-up member thus greatly increases the speed by which the belt will now be wound around the wind-up member. As a result, the longitudinal speed of the distal end 56 of the belt 52 greatly increases and is translated into greater speed in retracting the restraining sheath 40 and deploying the stent. Finally, FIGS. 12 and 13 show additional rotation of the thumbwheel 46 which allows the belt 52 to start winding about itself and the composite outer edge. This particular embodiment shows just one way in which the speed-increasing member can be associated with the wind-up member to progressively increase the speed of deployment.

It is noted that the smaller radius of the drum 48 continues for about 180° and then "ramps up" to the larger radius. It should be appreciated that the amount of "run" of this smaller radius could be varied, as desired, in order to obtain the required mechanical advantage provided by this mechanism. The "ramp" portion of the drum, i.e., the spiral configuration, can also be profiled for any desired transition, i.e., gradual, abrupt, constant, stepped and the like. Additionally, the effective outer radius resulting from a rotation of 360° is shown producing about a doubling of the radius of the drum. It should be appreciated that a smaller or larger increase of the radius could be obtained after 360° of rotation, or at a rotation less than 360°. Also, the final diameter can be in a shape that is not necessarily constant diameter, for example, a square, hexagonal and other non-circular shapes. Also, one or multiple cams could be used to obtain the desired radius and shape of the drum.

The speed-increasing member is shown as linked cams which quickly or slowly increases the outer radius of the drum. It should be appreciated that other components could be used to form the speed-increasing member. For example, a single, flexible component could be attached to the drum to quickly increase its outer radius. In this aspect, the flexible component would wrap around the drum's outer edge as the belt 52 is being wound onto the drum. The flexible component would wrap around with the belt and be "sandwiched" between the drum and the belt windings to rapidly or slowly increase the radius. Such a component could be good for multiple or only portions of the drum's revolution.

Figure 14A:
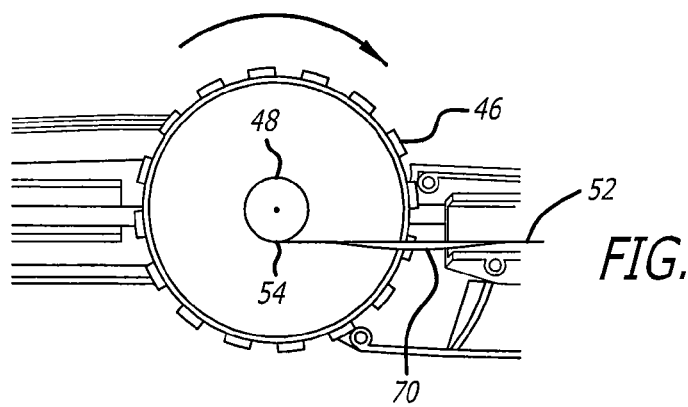
FIG. 14A is a side elevational view showing one particular embodiment of a thumbwheel, drum, belt and belt cam made in accordance with the present invention.
Figure 14B:
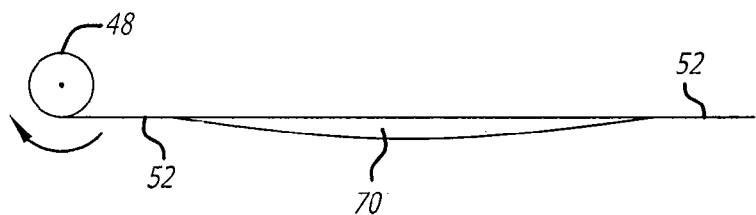
FIG. 14B is a side elevational view showing only the drum, belt and belt cam of the embodiment of FIG. 14A.

Referring now to FIGS. 14A and 14B, another embodiment of the present invention is disclosed in which the actuation mechanism includes a speed-increasing member associated with the elongated member (the belt 52) rather than the wind-up member (drum 48) In FIG. 14A, the drum 48 is shown again with the drum plate 57 removed to better show the drum 48. In this particular embodiment, the drum 48 is shown having a circular diameter, rather than the spiral shape, disclosed in the embodiment of FIGS. 1-12. The belt 52 again has its first end 54 attached to the drum 48 with the distal end attached to the shuttle and restraining sheath (not shown in FIGS. 15A and 15B). Again, rotation of the thumbwheel 46 causes the drum 48 to rotate (here shown in the clockwise motion) in order to have the belt 52 wrap around the drum 48. As can be better seen in FIG. 14B, the belt 52 includes a speed-increasing member, disclosed as a cam 70, associated with the belt 52. Rotation of the drum 48 will causes this cam 70 to increase the effective radius of the drum 48 as the belt 52 is being wound there around. This cam 70 provides a component that has increased thickness which will allow the belt 52 to more quickly wrap around the drum as the cam increases the effective drum diameter. This cam 70 will become sandwiched between the drum and belt and will increase the speed by which the belt will be wound around drum 48. As can be seen in 14B, the cam 70 can be located along the length of the 52 such that initially only the belt 52 itself wraps around the drum. This allows the actuating mechanism to achieve a high mechanical advantage when the thumbwheel 46 is initially rotated to commence removal of the restraining sheath from the stent. Thereafter, once the static frictional forces have been overcome, then, speed in removing the remaining portion of the restraining sheath 40 is more desired to reduce the number of times that the thumbwheel has to be manipulated by the physician. Therefore, the cam 70 will begin to wrap around the drum and the belt windings to increase the speed by which the belt will be wound around the drum. As can be see in FIG. 14B, the cam 70 has varying thickness from its distal end to proximal end which will create a circular winding once the cam 70 is completely wound about the drum 48.

Figure 15A:
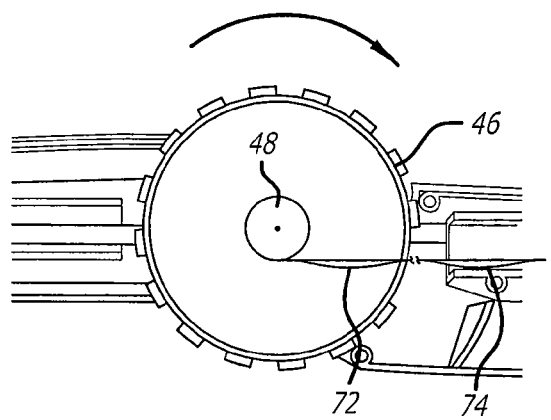
FIG. 15A is a side elevational view showing another particular embodiment of a thumbwheel, drum, belt and belt cam made in accordance with the present invention.
Figure 15B:
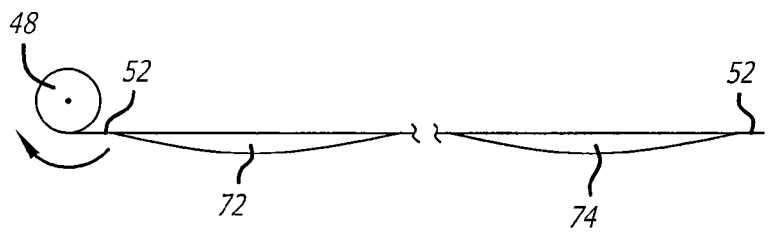
FIG. 15B is a side elevational view showing only the drum, belt and belt cam of the embodiment of FIG. 15A.

Referring now to FIGS. 15A and 15B, the actuating mechanism includes speed increasing members which consist of a plurality of cams 72 and 74 which can be associated at different locations all along the belt 52. In this fashion, a variable speed-increasing feature can be accomplished. A first cam 72 can be initially used to obtain increased speed after initial deployment begins. Thereafter, a length of the belt 48 itself can extend between the first cam 72 and the second cam 74. This results in the belt itself wrapping around the first cam 72 as the drum is rotated. Thereafter, once the proximal end of the second cam 74 reaches the drum, it will also add additional speed increasing features to the actuating mechanism by increasing the radius of the windings on the drum. Again, the speed by which the belt is wound around the drum will be translated to the speed that the retraining sheath is being retracted. It should be appreciated that any number of speed increasing members, such as cam 72 and 74, could be located on the belt to provide the desired variable speed. Moreover, the length, shape and thickness of the cams can be varied, as needed, to achieve the desired speed increase to the system.

Figure 16A:
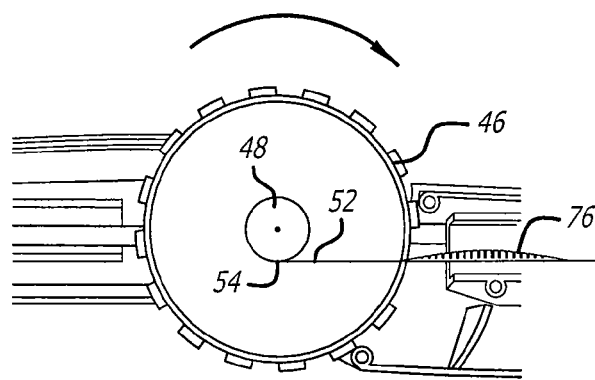
FIG. 16A is a side elevational view showing another particular embodiment of a thumbwheel, drum, belt and belt cam made in accordance with the present invention.
Figure 16B:
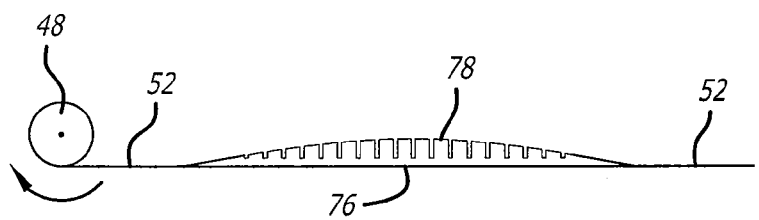
FIG. 16B is a side elevational view showing only the drum, belt and belt cam of the embodiment of FIG. 16A.
Figure 17A:
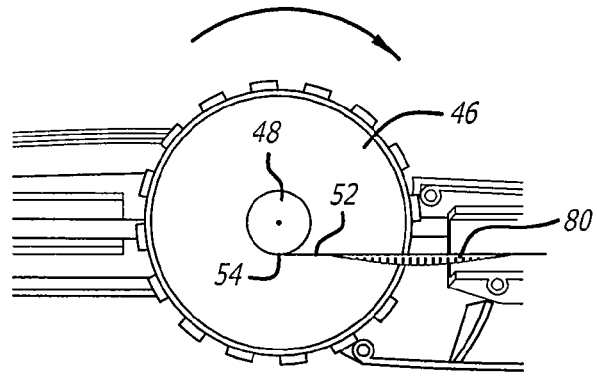
FIG. 17A is a side elevational view showing another particular embodiment of a thumbwheel, drum, belt and belt cam made in accordance with the present invention.
Figure 17B:
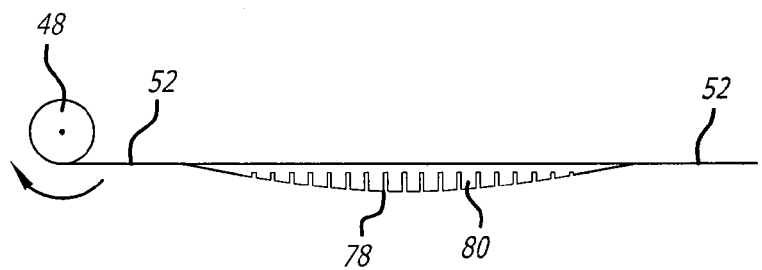
FIG. 17B is a side elevational view showing only the drum, belt and belt cam of the embodiment of FIG. 17A.

FIGS. 16A and 16B show another embodiment of the present invention including a cam 76 associated with the belt which includes a plurality of notches 78 that extend through the cam 76 to increase the flexibility of the cam as it is being rotated about the drum 48. Likewise, in FIGS. 17A and 17B, the cam 80 includes notches 78 which again provide greater flexibility as the cams 80 is being rotated about the drum.

It should be appreciated that the speed increasing member associated with the belt, namely the cams is closed in FIGS. 14A-17B could also be utilized in conjunction with a speed-increasing member associated with the wind-up member. In this regard, any of the belts and associated cams shown in FIGS. 14A-17B could be used with, for example, the spiral-shaped drum 48 disclosed in FIGS. 1-13 to further increase the speed by which the belt is wound by the actuating mechanism. The belt cams could be shaped in such a way that they would fit directly into the spiral-shaped drum 48 and produce the same effect as the drum cams. These belt cams could also be used with the combination of the spiral drum and drum cams disclosed in FIGS. 1-13. It should be appreciated that the size, shape and location of the belt cams can be varied, as needed, to achieve the desired type of deployment or activation of the device desired.

The handle assembly 22 shown in FIGS. 1-4 is particularly useful in deploying stents and other medical devices which have a long length since the shuttle assembly 36 can extend from almost distal end portion 24 to the proximal portion 82 of the handle. As a result, the length of retraction of the restraining sheath will be large enough to be fully retracted from the stent. As can be seen in FIGS. 3 and 4, the shuttle assemble 36 and belt 48 move within the channel 38 formed on one side of the handle assembly. The distal end 56 of the belt 52 is attached or coupled to the shuttle assembly 36 which, in turn, is coupled to the restraining sheath. The belt 48 also moves within a channel 84 (FIGS. 4 and 7) formed on another side of the handle assembly to prevent the belt from binding as it moves. A roller 86 located near the proximal portion of the handle assembly is utilized to allow the belt 52 to smoothly move from channel 38 to channel 84 without effecting its longitudinal speed.

It should be appreciated that in the disclosed embodiment, the restraining sheath 40 is shown as a elongate tubular member extending from the end of the shuttle assembly to the distal portion 44 which covers the stent. However, it is possible to utilize other components which can achieve the same function. For example, a short restraining sheath could be used to cover the medical device. A pull wire(s) which run the length of the catheter portion, shown in FIG. 2, could then be attached to the restraining sheath and the shuttle assembly 36. These pull wires, rather than a tubular member, would be moved proximally to retract the restraining sheath.

As can be seen in FIGS. 3 and 4, the belt 48 extends along the length of the handle assembly 22. It should be appreciated to those skilled in the art that the shuttle assembly could be eliminated. In this regard, the restraining sheath, or the pull wire(s) could be directly coupled to the belt.

It should also be appreciated that although the elongated member is shown as a flat belt, other components could be utilized besides a belt. For example, a wire could be utilized in place of the belt. In this regard, the wire would also be capable of being wrapping around the drum, with the cams increasing the speed by which the wire will be wrapped around the drum. Accordingly, the width of the drum may be required to be shortened to take into account a thinner wire. However, the same features of the present invention could be achieved using either a wire, belt or other elongate member.

FIGS. 18-22 show other embodiments of a wind-up member 90 which can be used in accordance with the present invention. Initially referring to FIGS. 18 and 19, the wind-up member 90 is shown configured with a speed increasing member formed as a substantially conical or cone-shaped portion 92 which allows the elongate member 94 to rapidly or slowly wind as the wind-up member 90 is being rotated. In this aspect, the elongate member 94 could be either a belt or wire which winds up along the conical portion 92 of the wind-up member 90. This conical portion 92 eliminates the need for drum cams to effectively increase the radius of the wind-up member 90.

Figure 18:
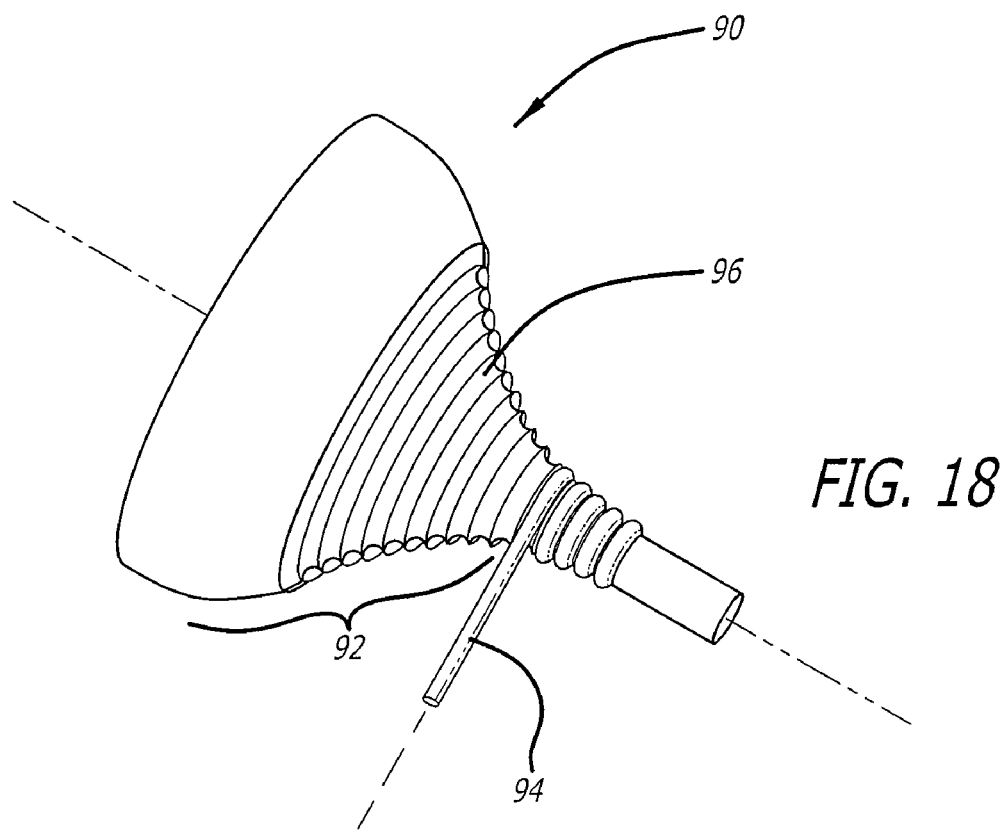
FIG. 18 is a side elevational view showing another particular embodiment of a wind-up member including a conical-shaped portion made in accordance with the present invention.
Figure 19:
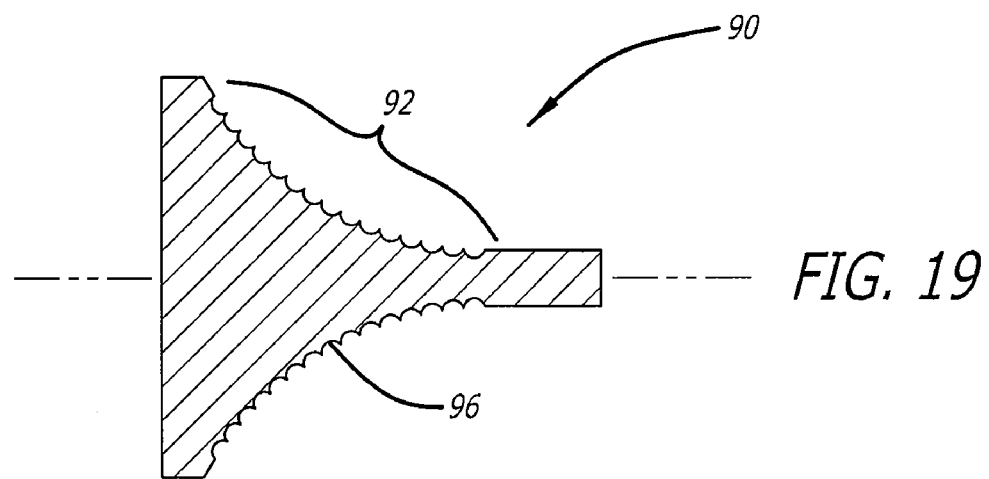
FIG. 19 is a cross-sectional view showing the particular profile of the conical portion of the wind-up member of FIG. 18.

As can be seen in FIGS. 18 and 19, the shape of the conical portion 92 could be varied to increase the speed by which the elongate member 94 will wind about the wind-up member 90. The conical portion 92 may include a groove 96 which extends around the conical portion 92. This groove 96 allows the elongate member 94 to easily wrap itself around the conical portion without slipping or bunching. Alternatively, the conical portion 92 could be made without a groove 96 if the elongate member is able to wrap itself properly about the conical portion 92 without slipping or bunching.

FIG. 18 shows one particular pattern that could be used to form the conical portion 92 of this wind-up member 90. Other configurations could also be utilized, as is disclosed in FIGS. 20-22. For example, in FIG. 20, the conical portion 92 initially has a small radius, like the embodiment of FIGS. 18 and 19, to provide increased mechanical advantage during the initial actuation of the wind-up member. The radius then quickly increases to enhanced the speed by which the elongate member (not shown in FIGS. 20-22) will wind. Accordingly, the speed by which the restraining sheath will be increased as well as the speed by which the medical device will be deployed.

Figure 21:
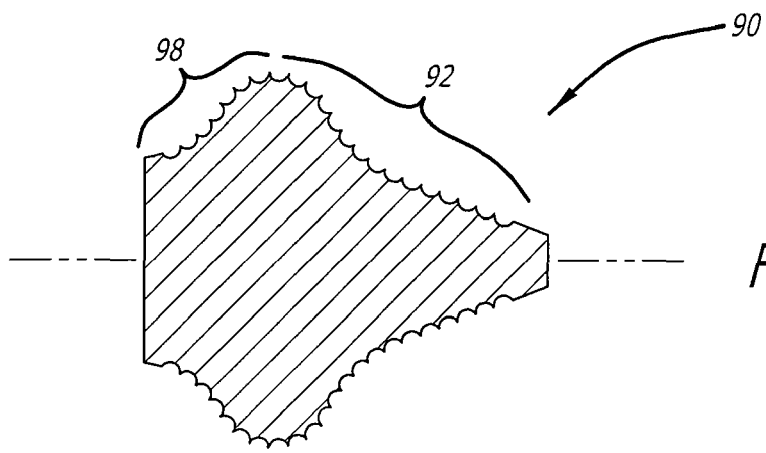
FIG. 21 is a cross-sectional view showing another particular embodiment of a wind-up member including a conical-shaped portion made in accordance with the present invention;.

FIG. 21 shows another unique profile that the conical portion 92 can be formed into to obtain varying speeds when winding up the elongate member. This profile shows a portion 98 of the wind-up member having a decreasing radius once the elongate member winds past the conical portion 92. This portion 98 of decreasing radius will slow down the rate at which the elongate member will be wound about this particular portion of the wind-up member 90.

Figure 20:
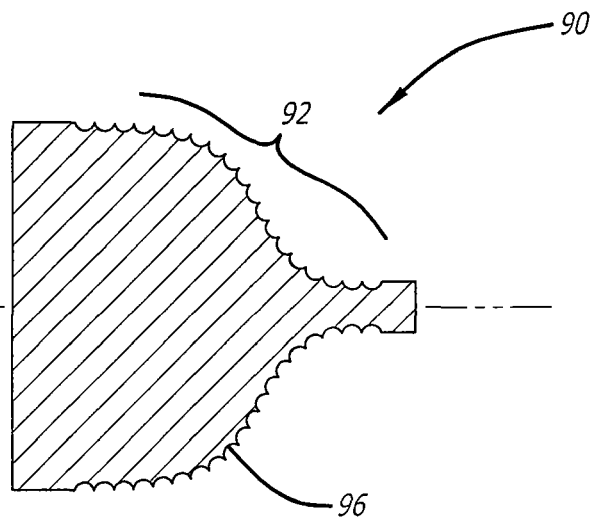
FIG. 20 is a cross-sectional view showing another particular embodiment of a wind-up member including a conical-shaped portion made in accordance with the present invention.
Figure 22:
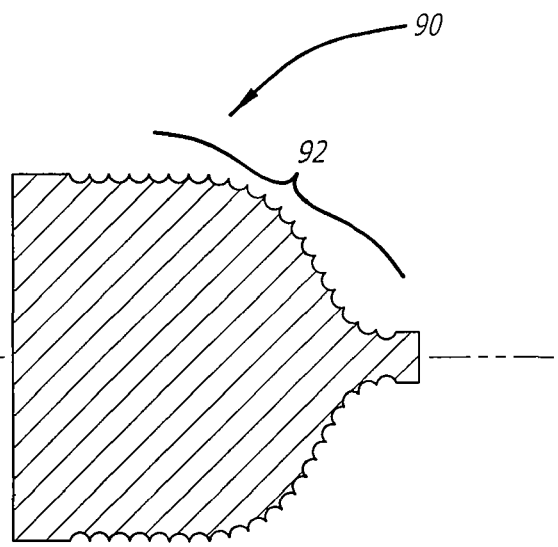
FIG. 22 is a cross-sectional view showing another particular embodiment of a wind-up member including a conical-shaped portion made in accordance with the present invention.

FIG. 22 shows a variation of the profile of the conical portion 92 which is shown in FIG. 20. In this particular embodiment, the conical portion 92 is very steep resulting in a rapidly increasing radius. As with the other embodiments, this rapidly increasing radius will dictate the speed by which the elongate member is wound about the wind-up member along with the speed by which the medical device will be deployed.

It should be appreciated that many different performance characteristics could be obtained by varying the radius of the wind-up member, as is shown in the above-disclosed embodiments. Accordingly, a multitude of the desired speed characteristics could be obtained by simply varying the radius of the wind-up member.

It should also be appreciated that although the actuating mechanism disclosed in the preferred embodiment is shown as a thumbwheel assembly which utilizes the user's thumb or finger to retract the thumb wheel, it is also possible to utilize other actuating mechanisms which can effect rotation of the wind-up member (drum 48). For example, a handle which utilizes a pistol-like structure having a retractable trigger could be utilized to rotate the wind-up member 48. For example, the trigger can be moved in a back and forth motion by the user's index finger which can be translated to rotation of the wind-up member. Such a trigger pistol like handle could include gears which engage the wind-up member to cause it to rotate. Additionally, a mechanism which utilizes linear motion could provide the actuating motion for deploying the stent. In such an embodiment, the actuating mechanism can include a component which is movable in a linear fashion by the user to cause the wind-up member to rotate. For example, a rack-and-pinion actuation mechanism attached to the component could cause the wind-up member to rotate. In this regard linear actuation would also cause rotation of the wind-up member. In such alternative designs, the speed-increasing members disclosed in the particular embodiments shown here would of course be incorporated with the rotatable wind-up member disclosed herein.

The drum 48 is shown in all of the embodiments as extending vertically. It should be appreciated that the drum could be position horizontally, or at any angle for that matter, within the handle. It should also be appreciated that the thumbwheel is shown directly coupled to the drum in these embodiments. Alternatively, the actuating mechanism could include gears which couple the thumbwheel to the drum. Therefore, the thumbwheel could be mounted vertically, with the drum mounted horizontally. Additionally, the gears could be selected to provides even additional initial mechanical advantage to the actuating mechanism.

It is to be understood that even though numerous characteristics and advantages of the present invention have been set forth in specific description, together with details of the structure and function of the invention, the disclosure is illustrative only and changes may be made in detail, such as size, shape and arrangement of the various components of the present invention, without departing from the spirit and scope of the present invention. It would be appreciated to those skilled in the art that further modifications or improvement may additionally be made to the delivery system disclosed herein without departing from the scope of the invention. Accordingly, it is not intended that the invention be limited, except as by the appended claims.

I claim:

1. A system for delivering a medical device within vasculature, comprising:
    a retractable sheath;
    a medical device retained by the retractable sheath; and
    a handle assembly including an actuating mechanism coupled to the sheath, the actuating mechanism including a flexible elongate member having one end coupled to the retractable sheath and another end coupled to a wind-up member, the wind-up member being rotatable to allow a portion of the flexible elongate member to wind thereon to effect longitudinal movement of the sheath, and a speed-increasing member associated with the actuating mechanism which increases the speed by which the sheath moves longitudinally as the flexible elongate member is wound about the wind-up member, wherein the wind-up member is a drum and the speed-increasing member is a first cam directly and pivotally connected to the drum and a second cam directly linked to the first cam.

2. The system of claim 1, wherein the flexible elongate member is a belt.

3. The system of claim 1, wherein the actuating mechanism further includes a thumbwheel coupled to the wind-up member for rotating the wind-up member.

4. The system of claim 1, wherein the wind-up member provides initial mechanical advantage to the actuating mechanism when the wind-up member is initially rotated by the user at a particular speed input and the speed-increasing member imparts a faster deployment speed in retracting the retraining sheath when the same input speed is applied by the user.

5. The system of claim 1, wherein the wind-up member has a first region and a second region, the first region having an outer edge with a substantially uniform radius and the second region having an outer edge with a radius that is larger than the radius found in the first region.

6. The system of claim 5, wherein the second region is formed by a ramp-like structure which forms a part of the drum.

7. The system of claim 5, wherein when a particular input speed is applied to the actuating mechanism, the first region provides an initial deployment speed and the second region provides an increase deployment speed when the same input speed is applied to the actuating mechanism.

8. A handle for delivering a medical device within vasculature, comprising:
    a body; and
    an actuating mechanism located in the body, the actuating mechanism including a belt having a first end and a second end, the second end of the belt being coupled to a rotatable, wind-up member upon which at least a portion of the belt is wound to cause the first end of the belt to effect longitudinal movement, the wind-up member being rotated via an actuating motion to cause the belt to wind therearound, and a speed-increasing member to increase the longitudinal speed of the first end of the belt as the belt winds around the wind-up member when a particular input speed is applied by the user to the actuating mechanism, wherein the wind-up member is a drum and the speed-increasing member is a first cam directly and pivotally connected to the drum and a second cam directly linked to the first cam.

9. The system of claim 8, wherein the actuating mechanism provides a mechanical advantage when the actuating mechanism is initially actuated by the user.

10. The system of claim 8, wherein the wind-up member has a first region and a second region, the first region having an outer edge with a substantially uniform radius and the second region having an outer edge with a radius that is larger than the radius found in the first region.

11. The system of claim 10, wherein the second region is formed by a ramp-like structure which forms a part of the drum.

12. The system of claim 10, wherein when a particular input speed is applied to the actuating mechanism, the first region provides an initial deployment speed and the second region provides an increase deployment speed when the same input speed is applied to the actuating mechanism.

13. A system for delivering a medical device within vasculature, comprising:
    a retractable sheath;
    a medical device retained by the retractable sheath; and
    a handle assembly including an actuating mechanism coupled to the sheath, the actuating mechanism including a flexible elongate member having one end coupled to the retractable sheath and another end coupled to a wind-up member, the wind-up member being rotatable and having a outer edge upon which a portion of the flexible elongate member winds thereon to effect longitudinal movement of the sheath, the outer edge of the wind-up member having varying radiuses to increase the speed by which the retractable sheath moves longitudinally as the flexible elongate member is being wound about the wind-up member, and a speed-increasing member directly attached to the wind-up member, the speed-increasing member having an outer edge upon which a portion of the elongate member winds about as the wind-up member rotates, the speed-increasing member further increasing the speed by which the sheath moves longitudinally as the flexible elongate member is being wound about the wind-up member and the speed-increasing member.

14. The system of claim 13, wherein the wind-up member has a first region and a second region, the outer edge of the wind-up member having a substantially uniform radius in the first region and the outer edge of the wind-up member having a radius in the second region that is larger than the radius found in the first region.

15. The system of claim 13, wherein the outer edge of the speed-increasing member extends from the outer edge of the wind-up member.

16. The system of claim 13, wherein the speed-increasing member is pivotally and directly attached to the wind-up member.

17. The system of claim 16, wherein the speed-increasing member extends over a portion of the wind-up member and the elongate member when the wind-up member is rotated.

18. The system of claim 13, further including a second speed-increasing member associated with the actuation mechanism.

19. The system of claim 18, wherein the second speed-increasing member is coupled to the first mentioned speed-increasing member.

20. The system of claim 19, wherein the second speed-increasing member includes an outer edge upon which a portion of the elongate member winds about as the wind-up member rotates, the second speed-increasing member further increasing the speed by which the sheath moves longitudinally as the flexible elongate member is being wound about the wind-up member, the first mentioned speed-increasing member and the second speed-increasing member.

21. The system of claim 13, wherein the speed-increasing member is a cam section.

22. The system of claim 20, wherein the second speed-increasing member is a cam section.

23. The system of claim 20, wherein the outer edges of the first mentioned and second speed-increasing members cooperate with the outer edge of the wind-up member to form a substantially circular disk.

24. The system of claim 13, wherein the actuating mechanism further includes a thumbwheel coupled to the wind-up member for rotating the wind-up member.

* * * * *